United States Patent [19]
Chang et al.

[11] Patent Number: 5,905,094
[45] Date of Patent: May 18, 1999

[54] SLURRY HYDROCARBON SYNTHESIS WITH REDUCED CATALYST ATTRITION AND DEACTIVATION

[75] Inventors: Min Chang, Warren; Constantine A. Coulaloglou, Mendham; Edward C. Hsu, Bridgewater, all of N.J.; Larry E. Pedrick, Houston, Tex.

[73] Assignee: Exxon Research and Engineering Co., Florham Park, N.J.

[21] Appl. No.: 08/955,131

[22] Filed: Oct. 21, 1997

[51] Int. Cl.$^6$ .................................................... C07C 27/00
[52] U.S. Cl. ............................................ 518/700; 518/715
[58] Field of Search ..................... 518/700, 715

[56] References Cited

U.S. PATENT DOCUMENTS

| | | | |
|---|---|---|---|
| 4,251,926 | 2/1981 | Bagley et al. | 34/57 A |
| 4,257,171 | 3/1981 | Johnson et al. | 34/57 A |
| 5,422,375 | 6/1995 | Rytter et al. | 518/700 |
| 5,527,473 | 6/1996 | Ackerman | 210/767 |

*Primary Examiner*—Paul J. Killos
*Assistant Examiner*—Jafar Parsa
*Attorney, Agent, or Firm*—Jay Simon

[57] ABSTRACT

A slurry hydrocarbon synthesis process with reduced catalyst attrition is achieved by injecting a synthesis gas comprising a mixture of $H_2$ and CO up into the reactive slurry with a gas distribution grid having gas injectors horizontally arrayed across, and vertically extending through, an otherwise gas and liquid impervious plate. The injectors have a throat with a gas pressure reducing orifice at one end, which is the bottom and gas entrance end, and the other end opening into an open cone in which the uprising gas contacts the slurry. Flow diverting means in the injectors prevents slurry from entering the throat and being attrited. The gas injectors do not protrude above the top surface of the plate and flat space is eliminated by means such as angular fillers, to prevent solids accumulation top of the tray.

17 Claims, 4 Drawing Sheets

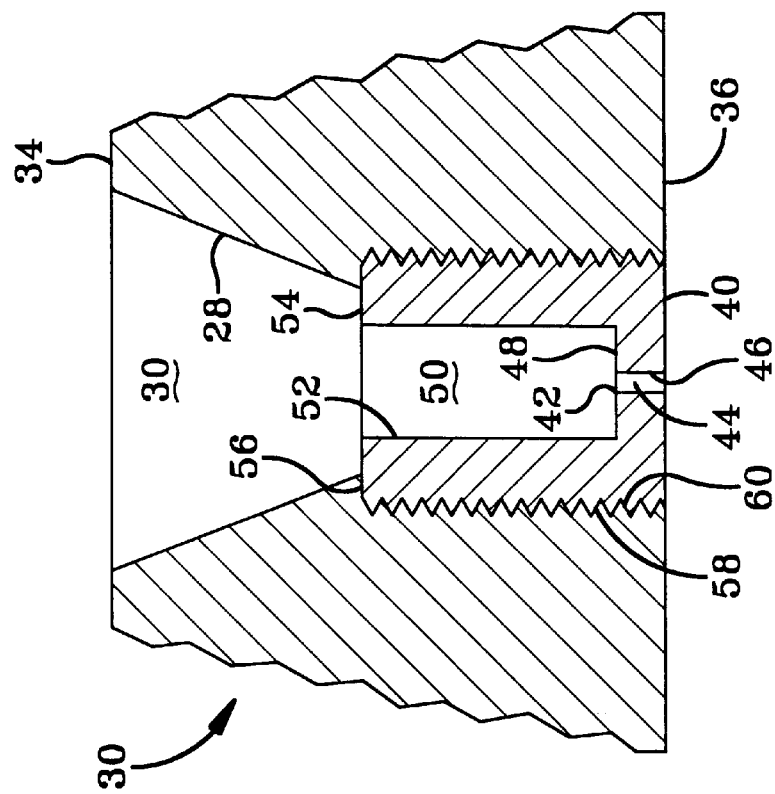
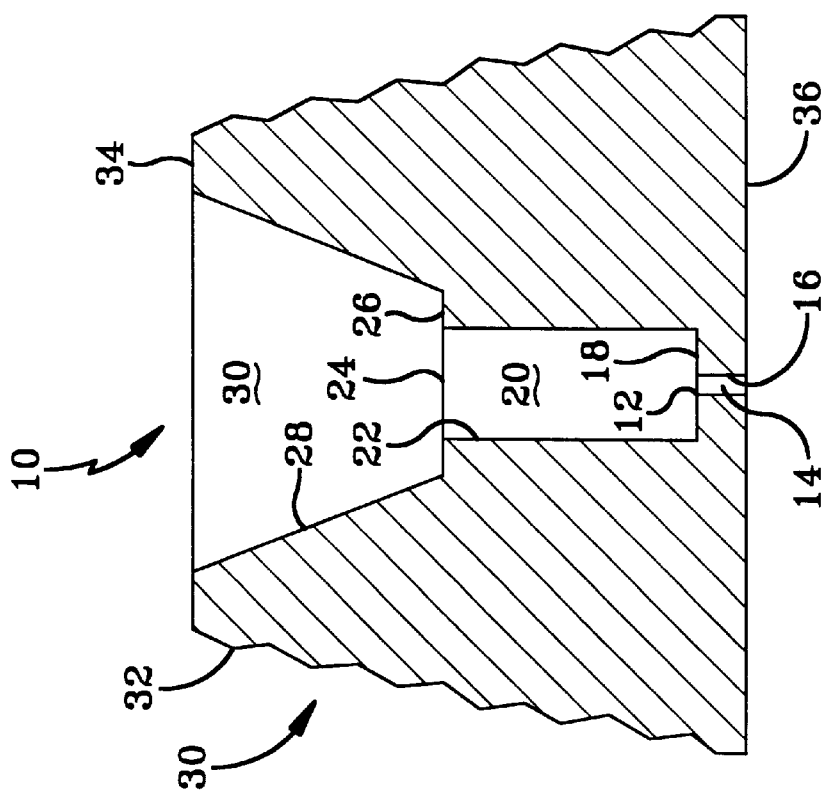

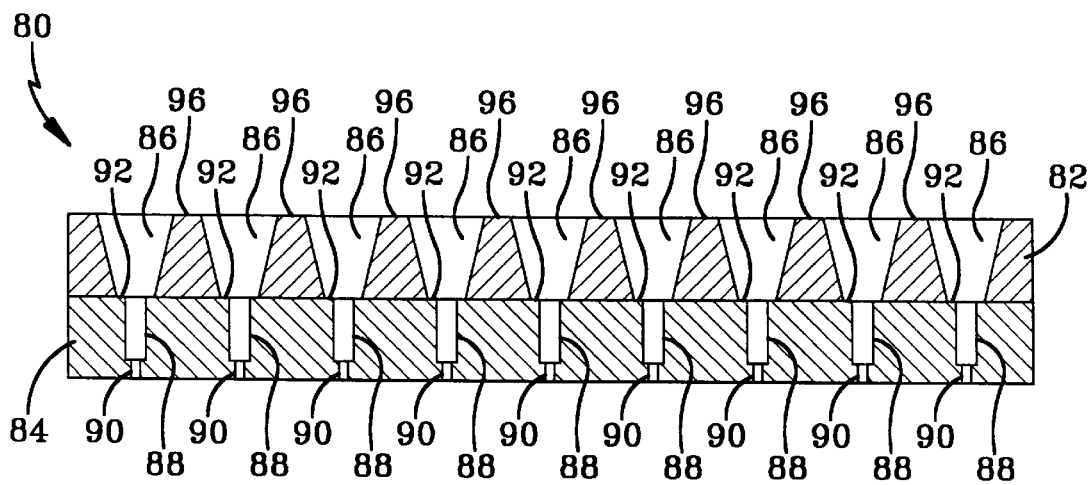
FIG-8(a)
FIG-8(b)
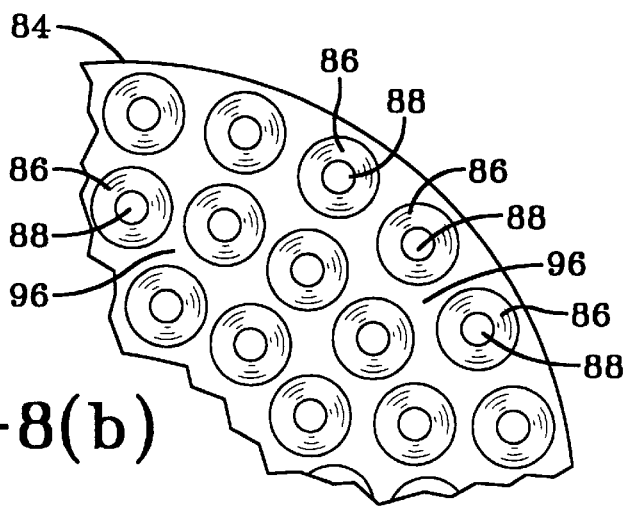
FIG-9
FIG-10
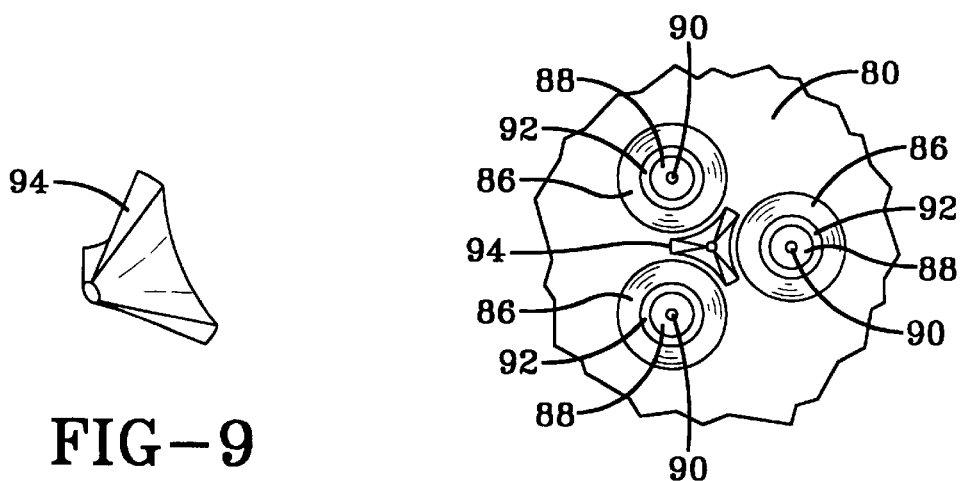

5,905,094

SLURRY HYDROCARBON SYNTHESIS WITH REDUCED CATALYST ATTRITION AND DEACTIVATION

BACKGROUND OF THE DISCLOSURE

1. Field of the Invention

The invention relates to slurry hydrocarbon synthesis. More particularly, the invention relates to a slurry hydrocarbon synthesis process in which the syngas is injected into the slurry with reduced catalyst attrition and deactivation using a gas distribution grid which comprises a plurality of throat and cone gas injectors extending through and arrayed across an otherwise gas and liquid impermeable tray.

2. Background of the Invention

Slurry hydrocarbon synthesis processes are known. In a slurry hydrocarbon synthesis (HCS) process, a synthesis gas (syngas) comprising a mixture of $H_2$ and CO is bubbled up through a slurry in a reactor in which the slurry comprises solid catalyst particles and gas bubbles in a hydrocarbon slurry liquid at reaction conditions effective to convert the syngas to hydrocarbons, at least a portion of which are liquid at the reaction conditions, and with the slurry liquid comprising these liquid HCS products. The catalyst comprises a suitable Fischer-Tropsch type hydrocarbon synthesis catalyst. Reactors which contain such a three phase slurry are sometimes referred to as slurry "bubble columns", as is disclosed in U.S. Pat. No. 5,348,982. The catalyst particles are typically kept dispersed and suspended in the liquid by the lifting action of the syngas bubbling up through the slurry and by hydraulic means. The gas is bubbled up into the slurry by pipe grids, a plurality of pipes opening up into the slurry, or by means of a gas distribution grid or tray which the gas injectors comprise a porous or perforated plate, or a plurality of bubble caps, tuyres, risers or other gas injection means arrayed across and extending through an otherwise gas and liquid impervious, horizontal metal plate or tray at the bottom of the slurry and over the plenum space at the bottom of the reactor. Problems associated with the use of gas injectors include catalyst particle attrition, injector plugging, deactivation of catalyst settling on the grid and catalyst falling down through the injectors into the plenum space below. Attrition causes catalyst loss through fines production and this results in catalyst loss and plugging units downstream of the reactor. It would therefore be an improvement to the art to use gas injecting means which reduce or eliminate any of these problems.

SUMMARY OF THE INVENTION

The invention relates to slurry hydrocarbon synthesis (HCS) process in which a synthesis gas (syngas) comprising a mixture of $H_2$ and CO is injected up into the bottom of the reactive slurry from a gas distribution grid which reduces catalyst attrition. The slurry comprises a particulate hydrocarbon synthesis catalyst and gas bubbles in a hydrocarbon slurry liquid which comprises products of the HCS reaction that are liquid at the reaction conditions. The $H_2$ and CO react in the presence of the catalyst at conditions effective to form hydrocarbons, at least a portion of which are liquid at the reaction conditions, with the liquid hydrocarbon products continuously removed from the reactor and upgraded to more valuable products, by one or more conversion operations. Catalyst attrition is substantially reduced by using a gas distribution grid comprising a plurality of throat and cone gas injectors arrayed across an otherwise gas and liquid impermeable gas distribution grid located at the bottom of the slurry. That is, the gas distribution grid comprises a plurality of the throat and cone gas injectors horizontally arrayed or distributed across, and vertically extending through, an otherwise gas and liquid impervious horizontal plate or tray located at the bottom of the slurry. In one embodiment, all or a portion of the gas injectors are formed as an integral part of the grid. The gas injector comprises a throat or elongated, hollow, first gas expansion zone open at both ends, with one end being a gas entrance having a bore through which gas is passed from outside the jet, past an orifice which is the exit of the bore, and into the throat, with the other, downstream end opening into an upwardly and outwardly extending second gas expansion zone, which may be cone-shaped. An internal shoulder at the junction of the throat and cone provides a flow diverting means, which directs slurry seeping down along the wall of the cone radially inward into the gas jet exiting the throat, to prevent catalyst attrition and throat plugging. In a typical injector of the invention, the inner diameter of this shoulder is substantially the same as that of the throat and its outer diameter peripherally terminates at the inner wall of the bottom of the cone. More specifically therefore, the process of the invention comprises reacting $H_2$ and CO gas in the presence of a solid, particulate hydrocarbon synthesis catalyst, and particularly a Fischer-Tropsch type of hydrocarbon synthesis catalyst, in a slurry at reaction conditions effective to form hydrocarbons from the gas, at least a portion of which are liquid at the reaction conditions, wherein the slurry comprises the catalyst and bubbles of the gas in a hydrocarbon slurry liquid comprising the liquid hydrocarbons formed by the reaction and wherein a syngas comprising a mixture of the $H_2$ and CO is injected up into the bottom of the slurry by means of a gas distribution grid located at the bottom thereof which comprises a plurality of gas injectors horizontally arrayed across, and extending vertically through, an otherwise gas and liquid impervious plate. The injectors of the invention each comprise an elongated, hollow, first gas expansion zone open at both ends (the throat), with one end being a gas entrance having a pressure reducing bore through which gas is passed from outside the jet into the throat, with the other, downstream end of the throat opening into an upwardly and outwardly extending second gas expansion zone which opens into the slurry and in which the gas contacts the slurry (the cone). A flow diverting means is located proximate the junction of said first and second zones for imparting a radially inward flow direction to slurry flowing from said second towards said first zone. The process of the invention is meant to include slurry hydrocarbon synthesis processes which synthesize oxygenated hydrocarbons such as methane and higher alcohols, ketones, acetic acid, dimethyl ether and the like, as well as the more commonly synthesized nonoxygenated and primarily paraffinic hydrocarbons.

It has been found that the absence of the shoulder, or flow diverting means in the gas injector, can result in significant and substantial disintegration of the particulate catalyst solids into fine particle sizes by attrition. These fines are carried up and out of the reactor in the overheads, and also pass through liquid filters into downstream units. This results in a continuous and substantial loss of catalyst and also forms sludge in downstream units which can clog the units and which must eventually be separated from the product. The pressure drop through the bore is determined by its diameter or cross sectional area, which is smaller than that of the throat. The aspect ratio and diameter of the throat are sized to (i) insure that the expanding gas jet flowing up through the throat contacts the inner throat wall before it exits the throat and enters the cone and, in combination with the orifice diameter, (ii) achieve the desired gas velocity in the cone where it contacts the slurry. This wall contacting in the throat is important to obtain a more uniform velocity profile of the gas stream entering the cone by allowing the velocity at the outer periphery of the gas jet to fully develop and to prevent flow perturbations and irregularities at the outer periphery of the jet which might otherwise result in catalyst particles and other solid particles weeping down into the throat, where they will be attrited by the higher velocity gas jet entering the throat through the narrow, smaller orifice. The throat has a length to diameter ratio (aspect ratio) of less than 10:1 and preferably less than 8:1 to prevent throat plugging by slurry solids. This aspect ratio must also be large enough for the outer periphery of the expanding gas jet to contact the inner wall of the throat before exiting it, and preferably make the contact a finite distance upstream of the throat exit, to provide a margin of safety (e.g., at least 10% of the throat length). It is preferred that the longitudinal axis of the bore, throat, shoulder and cone all be coincident. The angle of the interior cone wall is preferably greater than the angle of repose of the slurry solids, to prevent solids build-up in the cone. While in a preferred embodiment, the bore, throat, shoulder and cone all have a circular cross-section perpendicular to their longitudinal axis, other cross-sections may be employed if desired. A plurality of these injectors, vertically extending through and horizontally arrayed or arranged across a horizontal, and otherwise gas and liquid impermeable plate or tray at the bottom of the slurry, uniformly distribute the syngas up into the HCS slurry, with a fairly uniform pressure drop and concomitant uniform gas injection velocity across and through each gas injector in the tray. This is determined by the desired gas throughput into the slurry, the number of injectors in the tray, the diameter of the injector bore, and the gas pressure upstream of the injector bore.

Close packing of the injectors across the grid will substantially reduce the amount of flat surface on the top of the grid. In a further embodiment, no part of the injector extends up past the top of the grid plate. These two features minimize the amount of dead space on the grid for slurry solids to settle on. In a slurry (HCS) process at least a portion of the solids are the HCS catalyst particles and the reduced solids settling results in less catalyst deactivation. The gas distribution grid is typically located above the syngas reservoir or plenum area at the bottom of the reactor. The syngas feed is passed into a plenum under the grid which serves as a pressure damper and which, in combination with the diameter of the orifice in the gas jets, the number of jets and gas pressure, insures that the amount of syngas entering each injector in the grid is the same.

Gas passing through the pressure reducing bore and into the throat or first expansion zone, exits the orifice as a radially outwardly expanding gas jet which flows through the throat and contacts the inner wall before it enters the cone. This contact is important, as it results in more energy being directed to the outer periphery of the jet exiting from the throat and into the cone, or second expansion zone. This provides sufficient gas velocity and mass (energy) at the periphery of the jet exiting the throat to prevent slurry from seeping down into the throat where the particulate solids can be attrited into fines by the relatively high velocity gas jet entering the throat from the bore. It also reduces the difference in gas velocity between the outer periphery and the center of the jet, which further reduces particle attrition when the gas contacts the slurry. As the gas jet exits the throat, it doesn't contact the inner cone wall at the throat and cone junction, because of the annular shoulder. In one embodiment, the inner periphery of the shoulder is adjacent the inner wall of the throat at its exit and the outer diameter peripherally terminates at the inner cone wall at the bottom of the cone. The shoulder acts as a flow diverter for slurry seeping down the wall of the cone by imparting a radially inward direction to the downflowing slurry. Slurry which flows down along the interior cone wall reaches the shoulder, which forces the downcoming slurry radially inward to where it meets the upflowing, expanding jet exiting the throat, which carries weeping the slurry back up into the slurry body above. As the expanding gas jet travels up through the cone, it contacts the slurry and breaks up into bubbles which have a net upward velocity greater than can be achieved with bubble caps and the like. In a further embodiment, the orifice opens into a cone or chamfer, or other means (depending on the shape of the orifice and throat) which prevents unrestricted expansion of the gas jet as it enters the throat, thereby preventing back swirls and eddies from forming which can be drawn into the expanding gas jet and disturb or cause perturbations, such as ripples, and other flow disturbances at the outer jet periphery as it travels up the throat and into the cone and also cause fluctuations in the jet itself. Such perturbations can permit slurry solids to weep down into the throat where they are attrited by the incoming higher velocity gas jet. The cone or chamfer thus stabilizes the expanding gas jet and has also been found to be beneficial in clearing the throat of solids due to reductions in the gas flow.

BRIEF DESCRIPTION OF THE DRAWINGS

FIG. 2 is a partial cross-sectional schematic of a gas injector of the invention as an integral part of a gas distribution grid.

FIG. 3 is a variation of the embodiment of FIG. 2.

FIGS. 8($a$) and 8($b$) respectively schematically illustrate a side view and a top plan view of an embodiment of a disk-shaped gas distribution grid of the invention.

FIG. 9 is a perspective of an arcuate, pyramidal spacer for eliminating flat areas on the top of the grid.

FIG. 10 is a top plan view of a portion of a grid showing the location of the pyramidal spacer.

DETAILED DESCRIPTION

Figure 1:
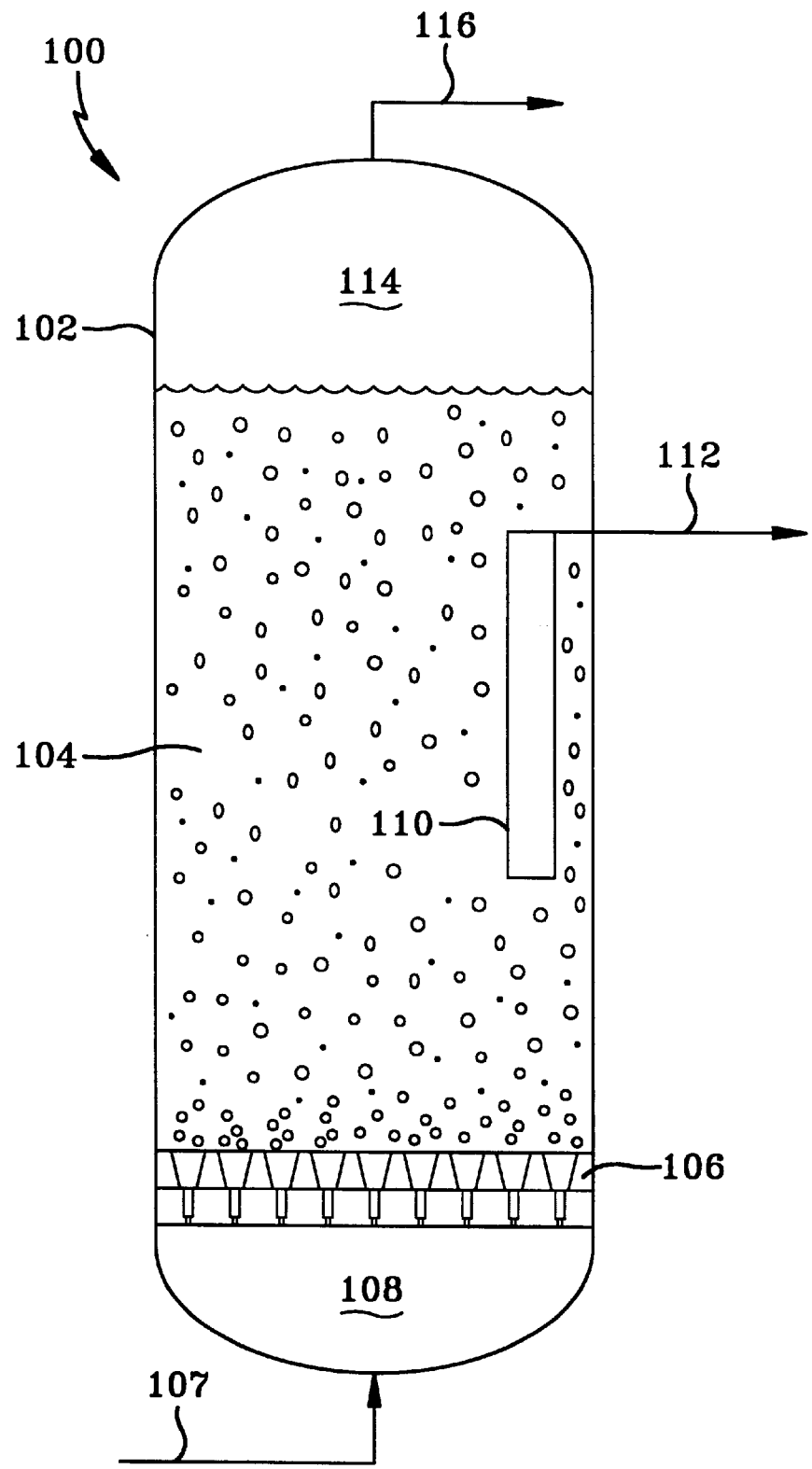
FIG. 1 is a simplified cross-sectional schematic of a slurry hydrocarbon synthesis reactor containing a gas distributing grid of the invention.

In a Fischer-Tropsch slurry HCS process, a syngas comprising a mixture of $H_2$ and CO is bubbled up into a reactive slurry in which it the $H_2$ and CO react in the presence of a Fischer-Tropsch type of hydrocarbon synthesis catalyst to form hydrocarbons and preferably liquid hydrocarbons. The mole ratio of the hydrogen to the carbon monoxide may broadly range from about 0.5 to 4, but which is more typically within the range of from about 0.7 to 2.75 and preferably from about 0.7 to 2.5. The stoichiometric mole ratio for a Fischer-Tropsch HCS reaction is 2.0, but there are many reasons for using other than a stoichiometric ratio as those skilled in the art know and a discussion of which is beyond the scope of the present invention. In a slurry HCS process the mole ratio of the $H_2$ to CO is typically about 2.1/1. Mole ratios of closer to 1:1 are used in the synthesis of the oxygenated products and dimethlyl ether referred to above. The syngas may be formed by any convenient means known to those skilled in the art, such as non-catalytic and catalytic partial oxidation, steam reforming and combinations of partial oxidation and steam reforming, such as autothermal reforming, and fluid bed syngas generation (FBSG) as is disclosed, for example, in U.S. Pat. Nos. 4,888,131 and 5,160,456. This need not be further explained.

As mentioned above, the reactive HCS slurry comprises catalyst particles and gas bubbles in a slurry liquid. The slurry liquid comprises hydrocarbon products of the synthesis reaction which are liquid at reaction conditions. While the temperature and pressure in the slurry can vary widely depending on the particular catalyst used and products desired, typical conditions effective to form hydrocarbons comprising mostly $C_{5+}$ paraffins, (e.g., $C_{5+}$—$C_{200}$) and preferably $C_{10+}$ paraffins, in a slurry HCS process employing a catalyst comprising a supported cobalt component include, for example, temperatures, pressures and hourly gas space velocities in the range of from about 320°–600° F., 80–600 psi and 100–40,000 V/hr/V, expressed as standard volumes of the gaseous CO and $H_2$ mixture (0° C., 1 atm) per hour per volume of catalyst, respectively. The syngas space velocity is determined primarily by the hydrocarbon production by the reactor and is typically greater than that required to disperse the solid catalyst particles in the slurry liquid. The slurry typically contains from about 10 wt. % to 70 wt. % catalyst solids, more typically from 30 wt. % to 60 wt. % and in some embodiments 40 wt. % to 55 wt. % is preferred. As mentioned above, the slurry liquid comprises hydrocarbon products which are liquid at the reaction conditions, along with minor amounts of other components. While catalyst particle sizes may broadly range from as small as 1 to as large as 200 microns, a typical conventional Fe or supported iron catalyst will have a mean particle size of about 22 microns, while a catalyst comprising a catalytic metal such as cobalt composited with or supported on titania will typically have a mean particle size of about 63 microns. However, such catalysts will also include fine particles as small as 1 micron and the constant agitation and mixing of the catalyst particles in the slurry results in particle size reduction through attrition. This also produces fines having a particle size of from about 1 to 10 microns. It is not easy to filter out fine particles. The process of the invention reduces catalyst fines generation, catalyst deactivation resulting from flat surfaces on the tray and weeping of slurry down through the tray and into the plenum space below.

FIG. 1 is a simple cross-sectional schematic of a slurry HCS reactor useful in the process of the invention containing a gas distribution grid of the invention which is that illustrated in FIG. 8. Turning to FIG. 1, there is shown a slurry HCS reactor 100 comprising a cylindrical shell 102 containing a slurry 104 within, which is supported by a gas distribution grid 106 of the invention of the type illustrated in FIG. 8, except that for the sake of simplicity the gas injectors are not shown in great detail. The grid comprises one or more circular metal plates horizontally disposed over the plenum space 108 which supports the slurry above and which contains a plurality of the gas injectors horizontally arranged across the flat horizontal surface of the grid and extending vertically therethrough. The outer periphery of the grid forms a seal with the inner surface of the reactor. The hollow space or plenum 108 under the grid is both a gas reservoir and a damper to smooth out fluctuations in the feed gas pressure. The syngas feed enters the reactor in the plenum space 108 via feed line 107 and is distributed up into the slurry 104 through the gas injectors extending through the grid. The small circles represent gas bubbles and the solid circles the catalyst particles. A filtration means simply illustrated by box 110 immersed in the slurry separates the liquid hydrocarbon products of the synthesis reaction from the catalyst particles, with the liquid being withdrawn via line 112 and passed to further processing and upgrading. A liquids and solids disengaging space 114 in the top of the reactor collects the gas products of the hydrocarbon synthesis reaction and the unreacted syngas and passes them out of the reactor as tail gas via line 116 to further processing and product recovery and upgrading. By way of an illustrative, but non-limiting example, for a thirty foot diameter reactor, the grid may contain as many as ten thousand gas injectors with a pressure drop of up to about twenty pounds per square inch across each injector.

Figure 6A:
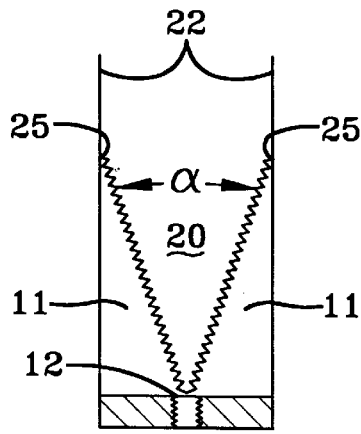
FIG. 6($a$) illustrates an expanding gas jet exiting the orifice and contacting the wall of the throat with a free expansion zone proximate the orifice, while FIG. 6($b$) shows the orifice opening out into a cone or chamfer to eliminate the free expansion zone of FIG. 6($a$).
Figure 6B:
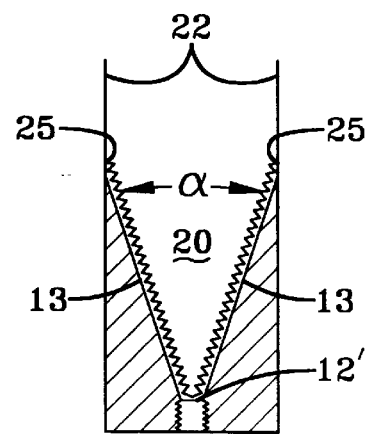

FIG. 2 schematically illustrates a vertical cross-section of a gas injector of the invention 10 as an integral part of a slurry reactor gas distributor grid 30 comprising a horizontal, disk-shaped steel plate 32, shown in partial form, which contains a plurality of gas injectors horizontally arrayed across the tray and extending vertically therethrough, of which only the one, 10, is shown for the sake of convenience. The top and bottom of the grid or plate are indicated at 34 and 36. The gas injector 10 extends vertically through the plate and comprises a cylindrical bore 14 defined by peripheral wall 16 which opens into a throat 20 through an orifice 12 which is the upper end of bore 14. The orifice opens up into throat 20 by means of shoulder or chamfer 18. While shoulder 18 is shown as horizontal and flat which means that orifice 12 is a sharp-edged orifice, in one embodiment it opens upward and outward from the perimeter of the orifice to the inner throat wall 22 as is explained below. In the latter case, the angular opening or chamfer extending from the orifice inhibits unrestricted expansion of the gas jet exiting the orifice up into the throat. Throat 20 is a cylindrical bore defined by a peripheral wall 22. Gas passes through bore 14 and emerges out of the upper end of the bore, which is the orifice, into throat 20 as a cone shaped, expanding gas jet which is illustrated in FIG. 6 and explained in detail below. Passage of the gas through the bore reduces its pressure, so that the gas pressure in the throat is less than that upstream of the bore (e.g., in the plenum below the grid). The gas jet entering the throat has an included angle ranging from about 10–20 degrees and more typically 15–20 degrees, as is known by those skilled in the art. The velocity of the expanding gas jet is reduced as it passes up through the first expansion zone or throat 20. The aspect ratio or length to diameter ratio of throat 20 is sized to permit the desired velocity reduction of the jet and, at the same time, insure that the expanding gas jet contacts the peripheral inner wall 22 of the throat, before it exits the throat at 24 and enters up into the second gas expansion zone or cone 30. In general, the aspect ratio will be at least 2 to insure that the expanding gas jet contacts the wall of the throat. On the other hand the maximum aspect ratio should not be larger than 8 or 10, to prevent throat plugging by the slurry solids, in the event of a reduction in gas flow. In the event of a reduction of the upstream gas pressure or a temporary cessation of the gas flow, the injector will fill up with the slurry solids and it has been determined that an aspect ratio greater than about 8 or 10 can prevent the gas from pushing out the solids when the pressure is restored, thereby plugging the injector and rendering it inoperable. It is also preferred that the expanding gas jet contact the throat wall sufficiently upstream of the throat exit to provide a factor of safety which can range anywhere from about 25% to about 75% of the throat length. As mentioned above, this contacting is an essential feature of the gas injector of the invention to insure sufficient gas velocity proximate the wall 22 at the throat exit 24, to prevent slurry weeping down the side of the cone from entering the throat. This also results in a more uniform horizontal gas velocity profile flow across the top or exit 24 of the throat. Throat 20 opens into the radially upward and outward extending second gas expansion zone 30 at the horizontal, circumferential flow diverting means illustrated as an annular shoulder 26. Zone 30 is a cone-shaped, and more specifically frusto-conical as defined by the frusto-conical peripheral wall 28 cut into the upper portion of the tray. In zone 30, the gas velocity is further reduced down to a level where it will not cause catalyst particle attrition, yet still be high enough to suspend the solids in the slurry and, in the case of a slurry reactor, provide a gas flow rate sufficient to achieve the desired reactor output. In the case of injecting synthesis gas into a slurry hydrocarbon synthesis reactor, the gas flow rate required for efficient hydrocarbon synthesis is typically greater that that required for catalyst suspension. The expanding gas jet contacts the slurry in zone 30 and breaks up into bubbles which rise up through the slurry. Slurry weeping down along the interior of the cone along wall 28 reaches shoulder 26 which imparts a radially inward direction and velocity to it and, as a consequence, the slurry is directed into the gas steam flowing up out of the throat exit 24. This lifts the downflowing slurry back up and into the slurry body above, while minimizing seeping of the slurry down into the throat where it will be attrited. It has been found that the use of the shoulder can result in as much as a twenty fold reduction in catalyst attrition. While it is believed that the most efficient cross-section of the orifice, throat and cone is circular, it is possible that in same cases one or more of these elements will have a cross-section other than circular. In the case of a cross-section other than circular, the diameter is taken as the equivalent diameter which is the square root of the cross-sectional area divided by pi, and the equivalent diameter is used in determining the aspect ratio of the throat.

Figure 4:
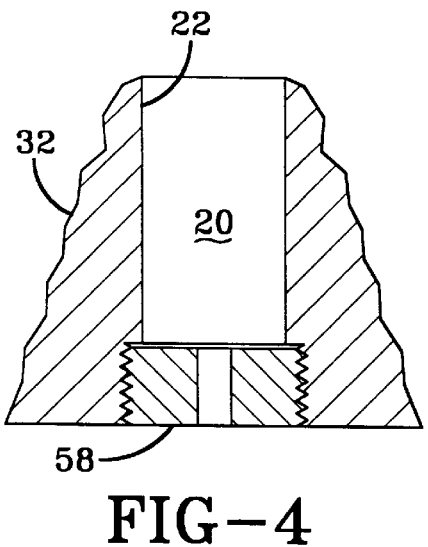
FIG. 4 briefly illustrates a replaceable orifice assembly for a gas injector of the invention.
Figure 5:
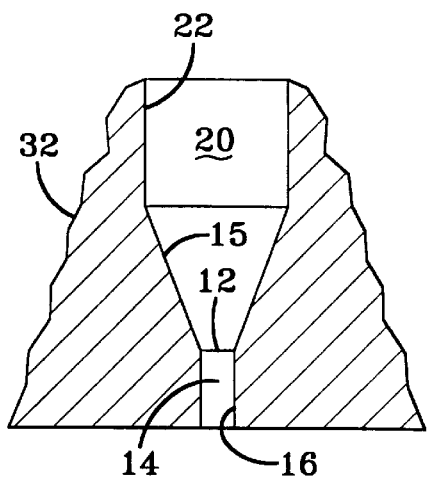
FIG. 5 schematically shows the orifice opening up into a cone or chamfer at the bottom of the throat of the gas injector.

FIG. 3 illustrates an embodiment of the invention similar to that of FIG. 2, but differs in that the bore and throat are a single, cylindrically shaped and externally threaded assembly 40 screwed into a mating threaded bore in the tray, indicated by screw threads 58. The bore 44, bore wall 46, orifice 42, throat 50 and wall 52 are identical to those shown in FIG. 2. However, the inner portion of the top 54 of cylinder 40 forms the flow diverting shoulder at the junction of the throat and cone. Assembly 40 screws up into the tray to where it meets with annular shoulder 56 at the bottom of the cone. That portion of the top of the cylinder 40 which does not contact the shoulder 56 forms the annular flow diverting means. Thus, in this embodiment the orifice and throat assembly are removably or detachably attached to the tray for facile replacement. Other embodiments will be apparent to those skilled in the art, such as a replaceable orifice assembly briefly illustrated in FIG. 4 and the like. Thus, in FIG. 4, a replaceable orifice assembly 58 is screwed up into a mating bore at the bottom of throat 20. FIG. 5 illustrates still another embodiment in which the bore 14 of FIG. 2 opens up into throat 20 by means of a chamfer or cone shaped wall 15. In this embodiment, the expanding gas jet exiting up out of orifice 12 is prevented from freely expanding out to the throat wall 22 proximate to the orifice 12 as it does in the embodiment of FIG. 3, by the cone or chamfer. This is illustrated in FIGS. 6(*a*) and 6(*b*). Thus, in FIGS. 6(*a*) and 6(*b*) an expanding, conical gas jet indicated as two wavy lines having an included angle α, exits orifice 12 and 12' and contacts the inner, cylindrical wall 22 of throat 20 at 25. In FIG. 6(*a*), space 11 surrounding the sharp-edged orifice 12 permits free expansion of part of the gas jet. Free expansion of the gas jet exiting orifice 12' is prevented by the cone or chamfer shaped wall 13 in the embodiment of FIG. 6(*b*). It has been observed that the presence of a cone or chamfer proximate the orifice prevents perturbations in the gas flow at the outer periphery of the expanding gas jet and also enables the gas to more easily blow out solids that may have filled up the throat during a lowering or cessation of the gas pressure upstream of the orifice. The cone angle should be determined experimentally for each case, but, in general, it will have an included angle less than the angle of repose of the solids in the slurry, to prevent slurry solids build-up on the interior cone wall. Generally, the included angle will be less than 140 degrees and in some embodiments, will be less than 90 degrees.

Figure 7:
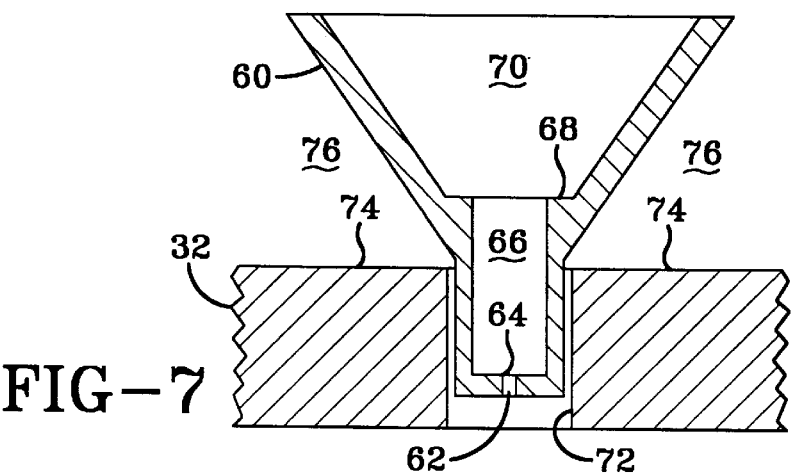
FIG. 7 schematically illustrates, in partial cross section, of another embodiment of a gas injector and grid of the invention.

Referring now to FIG. 7, a gas injector of the invention is shown being similar in most respects to that of FIG. 2, except it is not an integral part of a gas distribution tray. In this embodiment, the gas injector is a separate unit which is attached, by suitable means (e.g., screw threads) not shown, to a mating bore 72 extending through the tray from top to bottom. Thus, turning to FIG. 7, gas injector 60 comprises a cylindrical bore 62 which defines orifice 64 at its downstream end. Orifice 64 opens up into a larger diameter cylindrical bore 66 which is the throat or first expansion zone. Bore 66 opens up into a second, hollow, conical expansion zone 70 by means of annular shoulder 68, which is the slurry radial flow diverting means. The angle of the cone is less than the angle of repose of the solids in the slurry, to prevent solids accumulation on the inner cone wall. In this embodiment, even when a plurality of such injectors are horizontally arrayed across the surface of the tray, for each injector there will be an annular, flat surface on top of tray 32 below the cone, indicated at 74 for injector 60. In the case where the slurry solids comprise catalyst particles which deactivate when not in contact with the uprising gas, this space and the area 76 above 74 bound at the top by the cone is a dead space, in which catalyst particles will accumulate and deactivate. Hence, in such cases an embodiment similar to that of FIGS. 2 or 3 is preferred, unless other means are used to block off the dead space or pass gas through it to prevent catalyst accumulation.

FIGS. 8 (*a*) and 8 (*b*) respectively schematically illustrate a side view and a top plan view of an embodiment of a short cylindrical gas distribution grid or tray according to the invention, in which the grid contains a plurality of gas injectors of the invention horizontally arrayed across and extending through the grid in a manner similar to that shown in FIG. 2. However, in this embodiment the grid is formed of two separate circular, or disk-shaped plates 82 and 84, assembled and held together by suitable means such as screws or bolts (not shown). Upper plate 82 of the grid contains a plurality of conical cavities 86 extending therethrough which make up the second gas expansion zone for each injector. Lower plate 84 contains respective concentric mating throat and orifice cavities, indicated briefly as 88 and 90, extending through it and being coaxial with the longitudinal axis of each cone as shown. The throat diameter is smaller than the bottom of each respective and mating conical cavity in the top plate 82, so that the annular shaped flow diverting shoulder 92 is formed when the top and bottom plates are joined to form the completed grid. The top plan view is shown in greater detail in FIGS. 8 (*b*) and 10 explained below. No matter how close each cone is to its adjoining neighbors, there must be a flat space on top of the tray between the cones which is indicated as 96 in FIG. 8 (*b*). This space, on which catalyst will settle and deactivate, is readily reduced and even eliminated by an arcuate, pyramidal spacer 94 illustrated in perspective in FIG. 9 and in plan view in FIG. 10. In the embodiment shown, the top of the spacer is slightly flat and suitable means, such as a rounded top screw (not shown) is used to fasten the spacer onto the flat spaces. FIG. 10 shows more detail for the spacer and for the plan view of the injectors.

In an HCS process, liquid and gaseous hydrocarbon products are formed by contacting a syngas comprising a mixture of $H_2$ and CO with a suitable Fischer-Tropsch type HCS catalyst, under shifting or non-shifting conditions and preferably non-shifting conditions in which little or no water gas shift reaction occurs, particularly when the catalytic metal comprises Co, Ru or mixture thereof. Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to suitable products, by subjecting all or a portion to fractionation and/or conversion. By conversion is meant one or more operations in which the molecular structure of at least a portion of the hydrocarbon is changed and includes both noncatalytic processing (e.g., steam cracking), and catalytic processing in which a fraction is contacted with a suitable catalyst, with or without the presence of hydrogen or other coreactants. If hydrogen is present as a reactant, such process steps are typically referred to as hydroconversion and include, for example, hydroisomerization, hydrocracking, hydrodewaxing, hydrorefining and the more severe hydrorefining referred to as hydrotreating. Illustrative, but nonlimiting examples of suitable products formed by upgrading include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A hydrocarbon synthesis process which comprises:
   (a) injecting a synthesis gas comprising a mixture of $H_2$ and CO up into a slurry which comprises a solid, particulate hydrocarbon synthesis catalyst and gas bubbles in a hydrocarbon slurry liquid, wherein said synthesis gas is injected up into the bottom of said slurry by means of a gas distribution grid located at the bottom thereof which comprises a plurality of gas injectors horizontally arrayed across, and extending vertically through, an otherwise gas and liquid impervious plate, said injectors each comprising an elongated, hollow, first gas expansion zone open at both ends and having a pressure reducing bore at one end, which is the entrance end and with the other end opening into the bottom end of an upward and outward extending, hollow second gas expansion zone open at both ends, with a flow diverting means located proximate the junction of said first and second zones for imparting a radially inward flow direction to liquid flowing from said second towards said first zone, and
   (b) reacting said $H_2$ and CO in the presence of said catalyst in said slurry at reaction conditions elective to form hydrocarbons, at least a portion of which are liquid at said reaction conditions and wherein said slurry hydrocarbon liquid comprises said synthesized liquid hydrocarbons.

2. A process according to claim 1 wherein said catalyst comprises a Fischer-Tropsch catalyst.

3. A process according to claim 1 wherein said bore has a diameter smaller than that of said first expansion zone and wherein the aspect ratio of said first expansion zone is less than 10:1.

4. A process according to claim 3 wherein the aspect ratio of said first zone of said injectors is greater than 2:1.

5. A process according to claim 1 wherein at least a portion of each said gas injector is an integral part of said tray.

6. A process according to claim 5 wherein the longitudinal axis of said orifice and said first and second zones of said injectors are all coaxial.

7. A process according to claim 6 wherein said second zone does not extend above the top surface of said top plate.

8. A process according to claim 7 wherein flat space eliminators are present on flat surfaces at the top of said grid.

9. A process according to claim 1 wherein said flow diverting means comprises an annular shoulder whose outer periphery is adjacent the inner wall at said bottom of said second expansion zone.

10. A process according to claim 9 wherein said bore and first zone are cylindrical.

11. A process according to claim 10 wherein said second zone is frusto-concal.

12. A process according to claim 11 wherein said bore opens into said first zone by means of a chamfer to prevent unrestricted expansion of a gas jet entering said zone from said bore.

13. A process according to claim 1 wherein said hydrocarbon liquids are upgraded to more valuable product by one or more hydroconversion operations.

14. A hydrocarbon synthesis process which comprises:
(a) injecting a synthesis gas comprising a mixture of $H_2$ and CO up into a slurry which comprises a solid, particulate, Fischer-Tropsch hydrocarbon synthesis catalyst and gas bubbles in a hydrocarbon slurry liquid, by passing said gas through a pressure reducing zone to form an expanding gas jet which is passed through a first gas expansion zone in which it expands and contacts the inner wall of said zone, thereby providing more gas flow at the outer periphery of said jet which then exits said first zone and is passed through a second gas expansion zone in which said jet continues to expand and contact said slurry, with slurry which weeps down said second zone being diverted back into said uprising gas jet before it can enter said first zone, and
(b) reacting said $H_2$ and CO in the presence of said catalyst in said slurry at reaction conditions effective to form hydrocarbons from said gas, at least a portion of which are liquid at said reaction conditions and wherein said slurry hydrocarbon liquid comprises said synthesized liquid hydrocarbons which are withdrawn and upgraded to more valuable product by one or more hydroconversion operations.

15. A process according to claim 14 wherein said gas jet entering said first zone is not permitted to freely expand.

16. A process according to claim 14 wherein said pressure reducing zone and said first and second gas expansion zones are located in a gas jet and wherein a plurality of said jets are horizontally arrayed and vertically extend through an otherwise gas and liquid impermeable tray horizontally disposed at the bottom of said slurry in a reactor vessel to form a gas distribution grid.

17. A process according to claim 7 wherein said gas jet entering said first zone is not permitted to freely expand.

* * * * *